US009700621B2

(12) United States Patent
Levy et al.

(10) Patent No.: US 9,700,621 B2
(45) Date of Patent: Jul. 11, 2017

(54) METALLIC NANOPARTICLES, PREPARATION AND USES THEREOF

(75) Inventors: Laurent Levy, Paris (FR); Agnes Pottier, Paris (FR); Laurence Poul, Paris (FR); Laurence Maggiorella, Paris (FR)

(73) Assignee: NANOBIOTIX, Paris (FR)

( * ) Notice: Subject to any disclaimer, the term of this patent is extended or adjusted under 35 U.S.C. 154(b) by 38 days.

(21) Appl. No.: 13/383,049

(22) PCT Filed: Jul. 9, 2010

(86) PCT No.: PCT/EP2010/059871
§ 371 (c)(1),
(2), (4) Date: Jan. 31, 2012

(87) PCT Pub. No.: WO2011/003999
PCT Pub. Date: Jan. 13, 2011

(65) Prior Publication Data
US 2012/0203050 A1 Aug. 9, 2012

Related U.S. Application Data

(60) Provisional application No. 61/224,576, filed on Jul. 10, 2009.

(30) Foreign Application Priority Data

Jul. 10, 2009 (EP) .................................. 09165157

(51) Int. Cl.
*A61K 41/00* (2006.01)
(52) U.S. Cl.
CPC ................................ *A61K 41/0038* (2013.01)

(58) Field of Classification Search
CPC . A01N 59/16; A01N 5/00; A01N 5/10; A01N 5/1001; A01N 5/1014;
(Continued)

(56) References Cited

U.S. PATENT DOCUMENTS 6,955,639 B2 * 10/2005 Hainfeld et al. .................. 600/1
8,845,507 B2 * 9/2014 Levy .................. A61K 41/0038
424/490

(Continued)

OTHER PUBLICATIONS

Brun et al. ("Parameters governing gold nanoparticles X-ray radiosensitization of DNA in solution", Apr. 5 2009, Colloids and Surfaces B: Biointerfaces, Elsevier, Amsterdam NL, vol. 72 No. 1 pp. 128-134).*

(Continued)

*Primary Examiner* — Christine H Matthews
(74) *Attorney, Agent, or Firm* — Saliwanchik, Lloyd & Eisenschenk

(57) ABSTRACT

The present application relates to activable nanoparticles which can be used in the health sector, in particular in human health, to disturb, alter or destroy target cells, tissues or organs. It more particularly relates to nanoparticles which can generate a significantly efficient therapeutic effect, when exposed to ionizing radiations. The inventive nanoparticle is a metallic nanoparticle having, as the largest size, a size comprised between about 80 and 105 nm, the metal having preferably an atomic number (Z) of at least 25. The invention also relates to pharmaceutical compositions comprising a population of nanoparticles as defined previously, as well as to their uses.

13 Claims, 10 Drawing Sheets

(58) Field of Classification Search
CPC ...... A01N 5/1015; A01N 5/1028; A61N 1/05; A61N 2005/1098
USPC ...................................... 600/1–3; 378/64–65
See application file for complete search history.

(56) References Cited

U.S. PATENT DOCUMENTS

2004/0181114 A1    9/2004  Hainfeld et al.
2007/0031337 A1*   2/2007  Schulte .......................... 424/9.6

OTHER PUBLICATIONS

Brun, E. et al. "Parameters governing gold nanoparticle X-ray radiosensitization of DNA in solution" *Colloids and Surfaces B: Biointerfaces*, 2009, pp. 128-134, vol. 72, No. 1.

Zhang, S. X. et al. "Quantifying tumor-selective radiation dose enhancements using gold nanoparticles: a monte carlo simulation study" *Biomedical Microdevices*, 2009, pp. 925-933, vol. 11, No. 4.

Written Opinion in International Application No. PCT/EP2010/059871, Aug. 5, 2010, pp. 1-7.

Hoopes, P. J. et al. "Assessment of intratumor non-antibody directed iron oxide nanoparticle hyperthermia cancer therapy and antibody directed IONP uptake in murine and human cells" *Proc SPIE Int Soc Opt Eng.*, Feb. 23, 2009, pp. 1-17.

* cited by examiner

GOLD-15

GOLD-60

GOLD-80

GOLD-105

GOLD-15

GOLD-30

GOLD-60

GOLD-80

GOLD-105

REFERENCE

Gold nanoparticles GOLD-X nm (X=15, 32, 60, 80, 105 nm)

REFERENCE: gold nanoparticles with CFC structure to determine Lλ:

| Diameter (cm) | | $d_{hkl}$ | | Lλ |
|---|---|---|---|---|
| D1 | 1,90 | $d_{111}$ | 2,354 | 2,236 |
| D2 | 2,20 | $d_{200}$ | 2,039 | 2,243 |
| D3 | 3,10 | $d_{220}$ | 1,442 | 2,235 |
| D4 | 3,65 | $d_{311}$ | 1,229 | 2,243 |
| | | | | 2,239 |

Indexation of gold nanoparticles from example 1:

| Diameter (cm) | | Lλ | $d_{hkl}$ | Attribution |
|---|---|---|---|---|
| D1 | 1,90 | 2,239 | 2,357 | $d_{111}$ |
| D2 | 2,20 | 2,239 | 2,036 | $d_{200}$ |
| D3 | 3,20 | 2,239 | 1,400 | $d_{220}$ |
| D4 | 3,60 | 2,239 | 1,244 | $d_{311}$ |
| | | | | Gold CFC structure |

FIGURE 2B

METALLIC NANOPARTICLES, PREPARATION AND USES THEREOF

CROSS-REFERENCE TO RELATED APPLICATIONS

This application is the U.S. national stage application of International Patent Application No. PCT/EP2010/059871, filed Jul. 9, 2010, which claims the benefit of U.S. Provisional Patent Application No. 61/224,576, filed Jul. 10, 2009, the disclosures of which are hereby incorporated by reference in their entireties, including all figures, tables and amino acid or nucleic acid sequences.

FIELD OF THE INVENTION

The present application relates to activable nanoparticles which can be used in the health sector, in particular in human health, to disturb, alter or destroy target cells, tissues or organs. It more particularly relates to nanoparticles which can generate a surprisingly efficient therapeutic effect, when exposed to ionizing radiations such as X-Rays, γ-Rays, radioactive isotopes and/or electron beams. The inventive nanoparticle is a metallic nanoparticle having, as the largest size, a size comprised between about 80 and about 105 nm, the metal having preferably an atomic number (Z) of at least 25. The invention also relates to pharmaceutical compositions comprising a population of nanoparticles as defined previously, as well as to their uses.

BACKGROUND

Radiations of various forms such as X-Rays, gamma-Rays, UV-Rays, laser light, microwaves, electron beams as well as particle beams of, for example neutrons, and protons, have been used to treat cancer related issues. Some of said radiations have been used in such applications, in combination with radiation sensitive molecules. Electromagnetic and ionizing radiations are indeed capable in particular of breaking the DNA molecule of the cell, thereby killing cells and/or preventing said cell from growing and dividing. This effect is mainly due to indirect damages created in particular by electrons and/or high energy photons emitted after ionization that will be responsible for free radicals generation.

The term "Ionizing radiations" refers to highly-energetic particles or waves that can ionize an atom or molecule. Ionizing ability depends on the energy of individual particles or waves, and not on their number. A large flood of particles or waves will not, in the most-common situations, cause ionization if the individual particles or waves are insufficiently energetic. A typical ionizing radiation is a radiation, the energy of which is higher than 2 KeV.

Radiosensitization by gold nanoparticles (GNPs) has been identified as a promising approach for improving radiotherapy.

U.S. Pat. No. 6,955,639 (Hainfeld et al.) describes a method of enhancing X-Rays radiation effects using metal, in particular gold, nanoparticles, the size (diameter) of the metal core being preferably, for biodistribution reasons, in the range of 0.8 to 20 nm, more preferably 0.8 to 3 nm.

Herold et al. (Int. J. Rad. Biol. 76 (2000) 1357) indicate that gold nanoparticles of small size (~2 nm) should diffuse more homogeneously throughout the tumor mass.

Chithrani et al. (Nano Lett. 6 (2006) 662; Nano Lett. 7 (2007) 1542) showed a preferential penetration and accumulation of 50-nm diameter GNPs in Hela cells.

Chang et al. (Cancer Sci. 99 (2008) 1479) showed that, in a melanoma tumour-bearing mice model, 13-nm diameter GNPs in conjunction with a single dose of 25 Gy from a 6 MeV electron beam led to a more pronounced reduction of the tumor volume than in the control groups.

Zhang et al. (Biomed Microdevices (2009), 11:925-933) provides in silico datas (Monte Carlo simulation model) confirming that gold nanoparticles can enhance the effective dose of radiation, but does not study the nanoparticle's size impact on such dose enhancement. This document refers to the 1.9 nm diameter-nanoparticles of Hainfeld in the context of radiation therapy (see page 930, right column), but provides no result which may be of help to accurately quantify a dose enhancement factor in a biological system (see Montenegro et al., J. Phys. Chem. A. 2009, 113, 12364-12369: "Monte Carlo Simulations and Atomic Calculations for Auger Processes in Biomedical Nanotheranostics"), in particular in a human being.

Inventors herein provide powerful nanoparticles, which are surprisingly able to achieve a more efficient perturbation, alteration or destruction of target cells in vitro, ex vivo and in vivo when said nanoparticles are exposed to ionizing radiations, than nanoparticles described in the prior art, as herein demonstrated.

The inventive nanoparticle is a metallic nanoparticle having advantageously, as the largest size, a size comprised between about 80 nm and about 105 nm, the nanoparticle being made of a metal having preferably an atomic number (Z) of at least 25. The advantageous properties of the herein described nanoparticles could not be extrapolated from the art which, in contradiction with the present invention, suggests the use of gold nanoparticles of small size to increase the dose enhancement factor [see in particular Brun et al. (Colloids and Surfaces B: interfaces, 72 (2009) 128-134: *"Parameters governing gold nanoparticle X-ray radiosensitization"*) who reveal the influence of the gold nanoparticles concentration]. The results appearing on FIG. 4(B) of Brun et al. in particular, reveal a dose enhancement factor increase when the size of gold nanoparticle decreases, for a given gold concentration (the gold content varying with the gold nanoparticle radius according to a factor 3).

For a given metal concentration and a given ionizing radiation absorption ability, the metallic nanoparticles herein described, the size of a typical metallic nanoparticle being preferably between about 80 nm and about 105 nm, are responsible for an increased therapeutic efficacy (ability to generate target cells damages) when compared to nanoparticles of smaller sizes, in particular when compared to nanoparticles having a size of 60 nm or less.

For a given metal concentration and an equivalent X-Rays attenuation at cellular level, the metallic nanoparticles herein described exhibit a stronger ability to kill cells and/or prevent their division.

Another feature exhibited by the herein described nanoparticles, is their ability, when exposed to ionizing radiations, to generate a therapeutic effect when in contact with target cells. In other words, the therapeutic efficiency observed under irradiation does not require the nanoparticles cell uptake. Such a property is herein described for the first time.

Indeed, until now, the target cell uptake was believed, in the art, to be required for the nanoparticles to be able to generate efficient cellular lethal damages under irradiation (see for example Kong et al. (Small 4 (2008) 1537)).

The present invention thus goes against the prejudice of the all prior art leading the skilled person, mainly for biocompatibility, biodistribution, and cell uptake reasons, to the use, in terms of medical applications, of nanoparticles with a diameter from about 1 to 20 nm, at most 60 nm, with a particular and long-lasting interest for 50-nm nanoparticles (see for example Chithrani et al. (2006) and Chang et al. (2008)).

The nanoparticles of the present invention further advantageously allow a reduction in the amount of metal to be administered to a subject, as well as a reduction in the number of nanoparticles administration steps, to a minimum, in the context of a complete radiotherapeutic treatment protocol, thereby favouring their tolerance by the subject.

SUMMARY OF THE INVENTION

Inventors have now discovered that it is possible to disturb, alter or destroy target cells, tissues or organs, in particular abnormal cells or tissues, herein defined as benign cells or tissues, or diseased cells or tissues, such as pre-malignant or malignant cells (cancerous cells) or tissues (tumors), superficial or deep in the body, with a surprisingly increased efficiency, using a nanoparticle made of a metal having preferably an atomic number (Z) of at least 25, the largest size of said nanoparticle being comprised between about 80 nm and about 105 nm.

It is an advantage of the present invention to provide nanoparticles that are not noxious by themselves but can be safely employed, in appropriate conditions, to functionally disturb, alter or destruct target cells in an animal, preferably in a mammal, even more preferably in a human. The desired therapeutic effect of nanoparticles is indeed strictly dependent from their ionization, said ionization being generated by an ionizing radiation source which is itself advantageously controlled, in terms of quality and quantity, and used in a targeted, i.e., localized, way, by the man of the art.

The present invention indeed describes nanoparticles which can induce a cell perturbation, alteration or destruction in vitro, ex vivo or in vivo when said cell is exposed to ionizing radiations such as in particular X-Rays, gamma-rays (γ-Rays), radioactive isotopes, ion beams and/or electron beams.

The herein described nanoparticles are able to directly interact with incoming radiations and to generate a surprisingly efficient therapeutic effect, without it being necessary for the nanoparticles to be internalized by the target cells.

The nanoparticles according to the present invention can be covered with a biocompatible coating preferably favouring the nanoparticle stability in a physiological fluid as further described herein below.

The present nanoparticles can be used, if appropriate and preferred, in a targeted manner using for example a surface component enabling specific targeting of biological tissues or cells. They however do not require a targeting molecule to concentrate into the target cells or tissues.

The Enhanced Permeation and Retention ("EPR") effect is indeed responsible for passive accumulation into the tumor mass, after a given time following injection by the intravenous route (one possible route of administration) of the nanoparticles. It has indeed been observed that the tumor vessels are quite distinct from normal capillaries and that their vascular "leakiness" encourages selective extravasation of nanoparticles not usual in normal tissues. The lack of effective tumour lymphatic drainage prevents clearance of the penetrant nanoparticles and promotes their accumulation. The present nanoparticles are thus able to successfully target primary as well as metastatic tumors after intravenous administration.

The present nanoparticles can also be advantageously administered through intratumoral, or intra-arterial route.

It is therefore an object of the present invention to use a nanoparticle according to the present invention or a population of such nanoparticles to alter or destroy a target cell, tissue or organ.

Particular embodiments herein disclosed relate to the use of a population of metallic nanoparticles to prepare a pharmaceutical composition intended to perturb, alter or destroy target mammalian cells when said cells are exposed to ionizing radiations, wherein the nanoparticles are made of a metal having an atomic number (Z) of at least 25 and the mean largest size of the nanoparticles of the population is between about 80 and 105 nm, and to the corresponding methods of treatment.

Products according to the present invention, in particular nanoparticle and population of metallic nanoparticles, for use in the treatment of cancer, are in particular herein disclosed.

Another embodiment is based on a pharmaceutical composition, in particular, as will be apparent from the all description, a pharmaceutical composition intended to perturb, alter or destroy target cells in a mammal when said cells are exposed to ionizing radiations, said pharmaceutical composition comprising a population of metallic nanoparticles, as herein defined, and a pharmaceutically acceptable carrier or excipient, wherein the nanoparticles are made of a metal having an atomic number (Z) of at least 25 and the mean largest size of the nanoparticles of the population is between about 80 and 105 nm.

Another embodiment relates to the use of a nanoparticle, a population of metallic nanoparticles or composition according to the present invention, to prevent or treat a cancer or to alleviate the symptoms of a cancer in an animal, when said animal is exposed to radiations, in particular to ionizing radiations as herein defined.

The present disclosure in particular encompasses a method for preventing or treating a cancer or for alleviating the symptoms of a cancer in a subject, the subject being an animal, in particular a mammal, preferably a human, by administering a metallic nanoparticle, a population of metallic nanoparticles or a composition comprising a population of such nanoparticles according to the present invention, to the subject, and exposing said subject to radiations, in particular to ionizing radiations.

In another aspect, the present disclosure provides kits comprising any one or more of the herein-described products, i.e., nanoparticles and compositions, together with a labeling notice providing instructions for using the product(s).

BRIEF DESCRIPTION OF THE DRAWINGS

FIG. 1A shows the Transmission Electronic Microscopy (TEM) images of the gold nanoparticles described in Table 1 (see example 1).

FIG. 1B shows the size distribution of the gold nanoparticles (GNPs) described in Table 1.

FIGS. 2A and 2B: The crystalline structure of the as prepared gold nanoparticle is determined by electronic diffraction.

FIG. 2A shows the electronic diffraction pattern of reference nanoparticles (gold nanoparticles with Cubic Face Center structure are used as reference to establish the camera constant (Lλ) of the transmission electronic microscope) and of gold nanoparticles (GNPs) from example 1.

FIG. 2B reports the indexation of the gold nanoparticles (from example 1), electronic diffraction pattern showing a Cubic Face Center (CFC) structure of the gold nanoparticles.

Indexing the electronic diffraction pattern consists in the following steps:

1) Establishing the camera constant from electronic diffraction pattern of the reference,
2) Measuring the ring diameter (D1, D2, Dn) of electronic diffraction pattern of the gold nanoparticles from example 1,
3) Calculating the $d_{hkl}$, using the expression $d_{hkl}=L*\lambda/(Dn/2)$,
4) Using existing structure data base to index each ring.

Figure 3A:
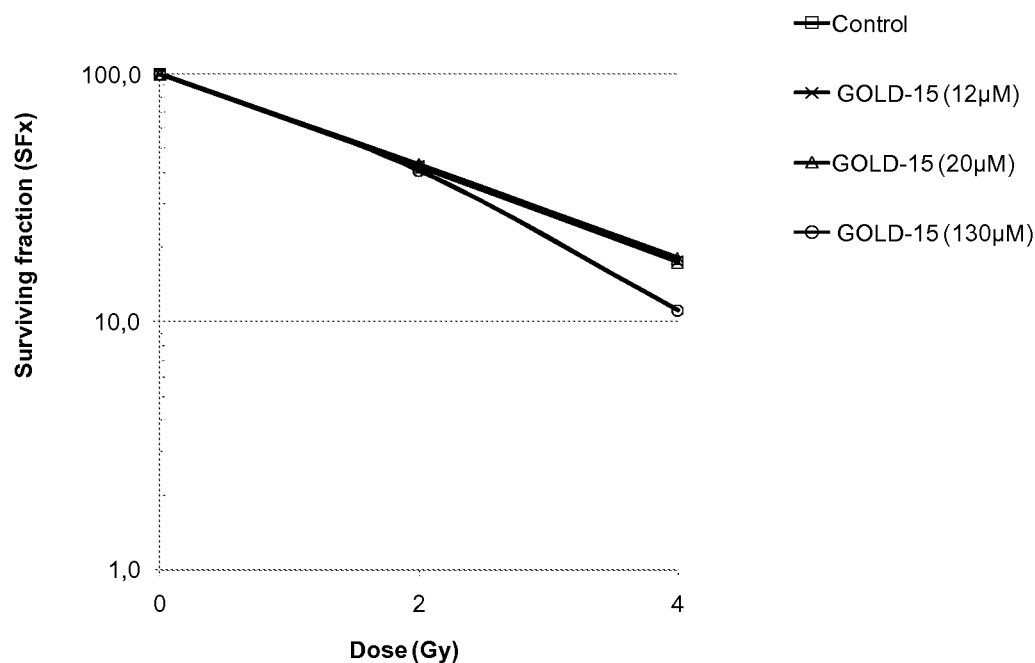
Figure 3B:
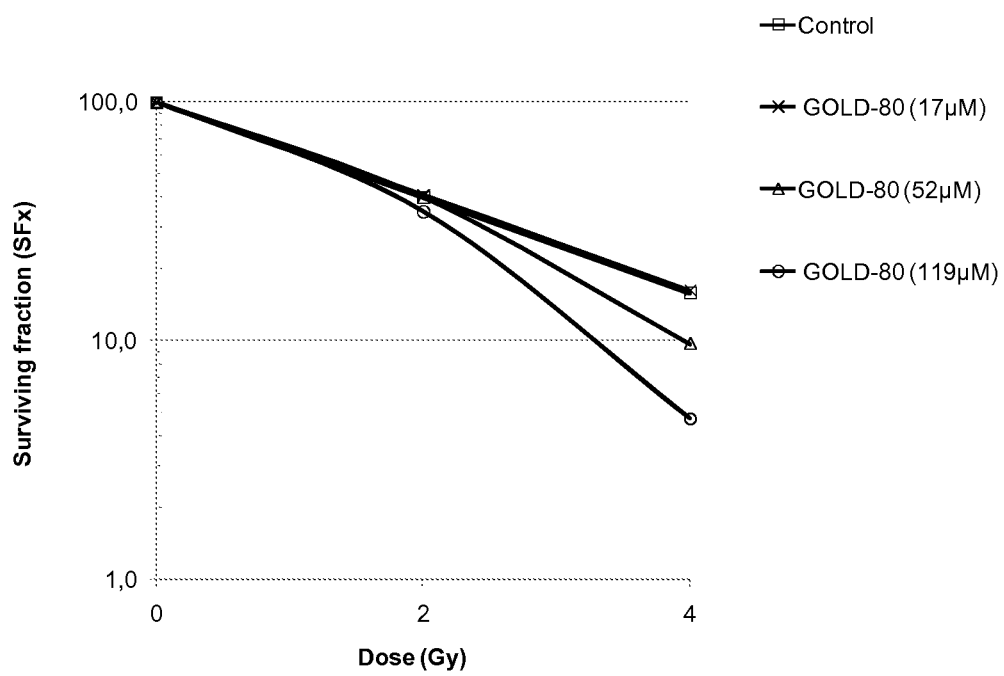

FIGS. 3A and 3B:

FIG. 3A shows clonogenic survival assays using HT29 colon cancer cells irradiated with a 200 KVp X-Ray energy beam, in the absence (negative control) or in the presence of 12 μM, 20 μM and 130 μM of gold at cellular level for gold nanoparticles with a particle size of 15 nm (GOLD-15 from example 1). Irradiation dose varies from 0 (no irradiation) to 4 Gy.

Negative control with HT29: square dots
Gold-15 nanoparticles with HT29 12 μM: cross dots
Gold-15 nanoparticles with HT29 20 μM: triangle dots
Gold-15 nanoparticles with HT29 130 μM: circle dots FIG. 3B shows clonogenic survival assays using HT29 colon cancer cells irradiated with a 200 KVp X-Ray energy beam, in the absence (negative control) or in the presence of 17 μM, 52 μM and 119 μM of gold at cellular level for gold nanoparticles with a particle size of 80 nm (GOLD-80 from example 1). Irradiation dose varies from 0 (no irradiation) to 4 Gy.

Figure 4A:
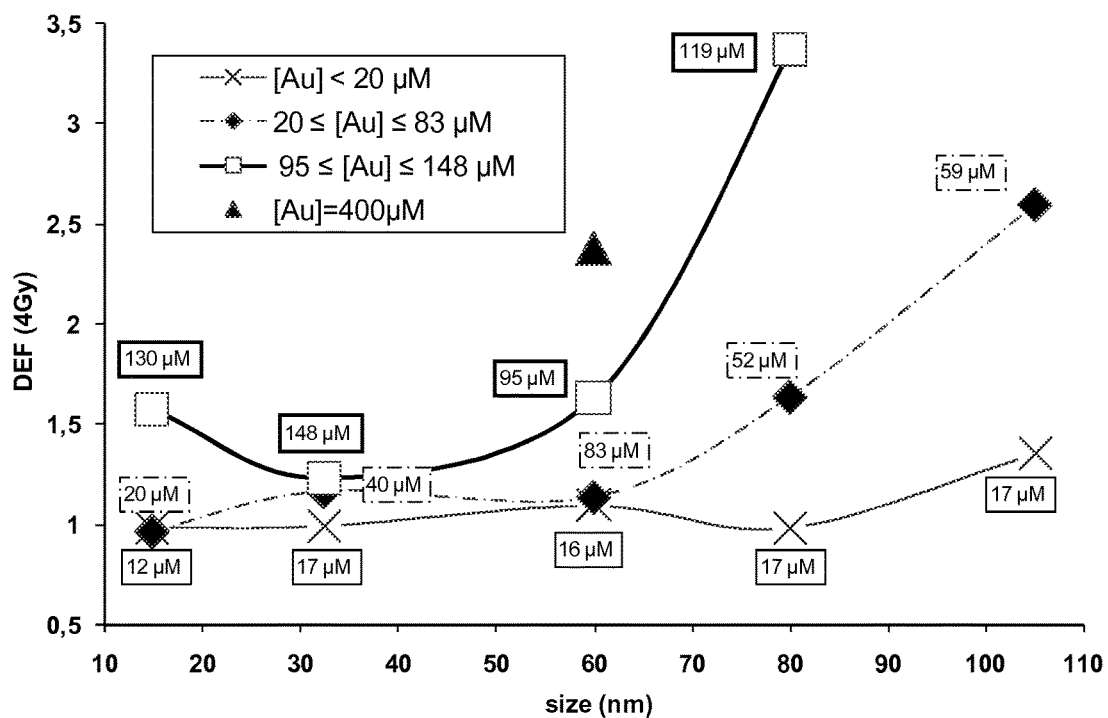
Figure 4B:
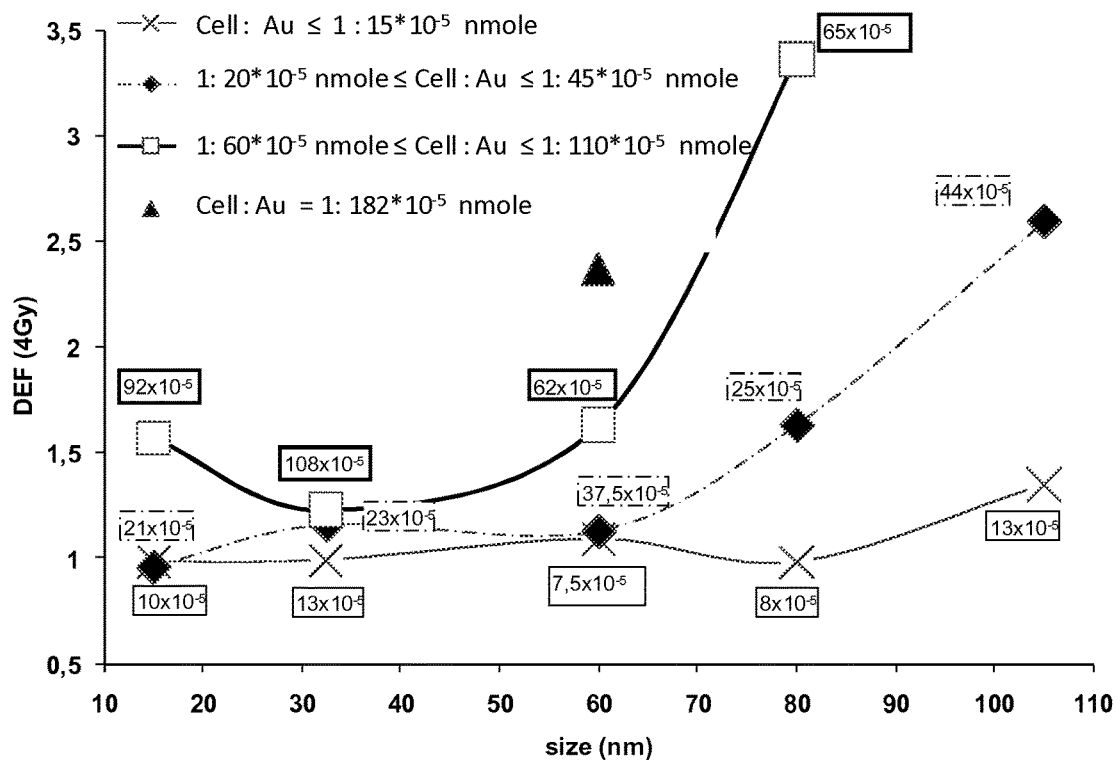

Negative control with HT29: square dots
Gold-80 nanoparticles with HT29 17 μM: cross dots
Gold-80 nanoparticles with HT29 52 μM: triangle dots
Gold-80 nanoparticles with HT29 119 μM: circle dots FIGS. 4A and 4B: Effect of gold nanoparticles size on the Dose Enhancement Factor (DEF) for similar gold concentration at cellular level, also herein identified as gold concentration per target cell.

FIG. 4A

Gold (Au) concentration at cellular level is expressed in μM.

Gold concentration below 20 μM ([Au]<20 μM): cross dots
Gold concentration between 20 μM and 83 μM (20 μM≤[Au]≤83 μM): diamond dots
Gold concentration between 95 μM and 148 μM (95 μM≤[Au]≤148 μM): square dots
Gold concentration at 400 μM ([Au]=400 μM): triangle dot

FIG. 4B

Figure 5A:
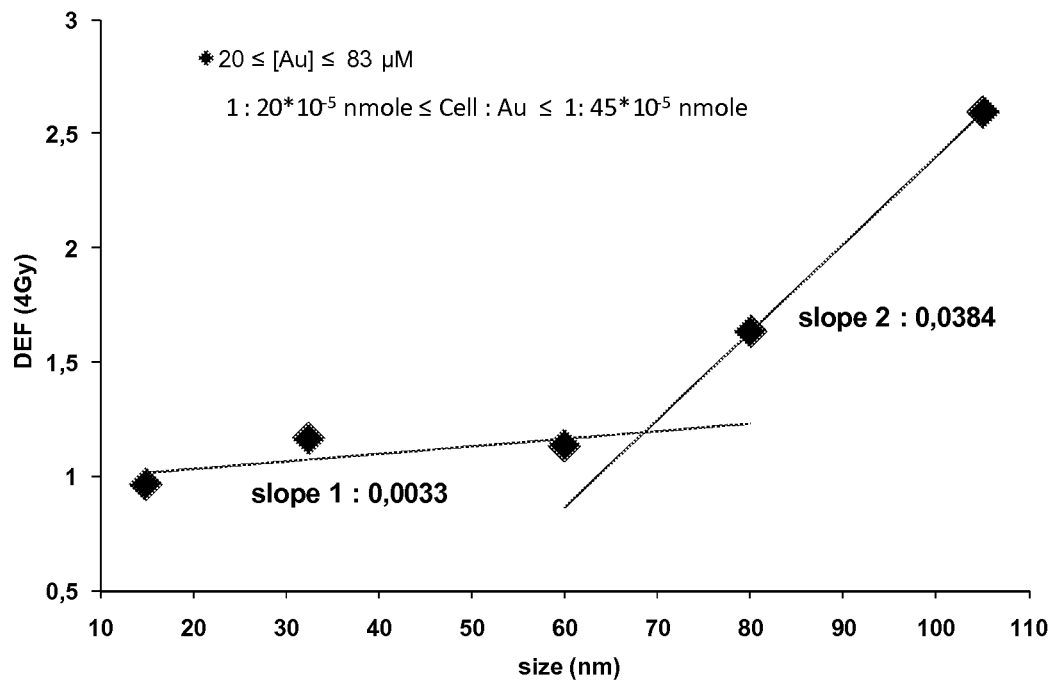
Figure 5B:
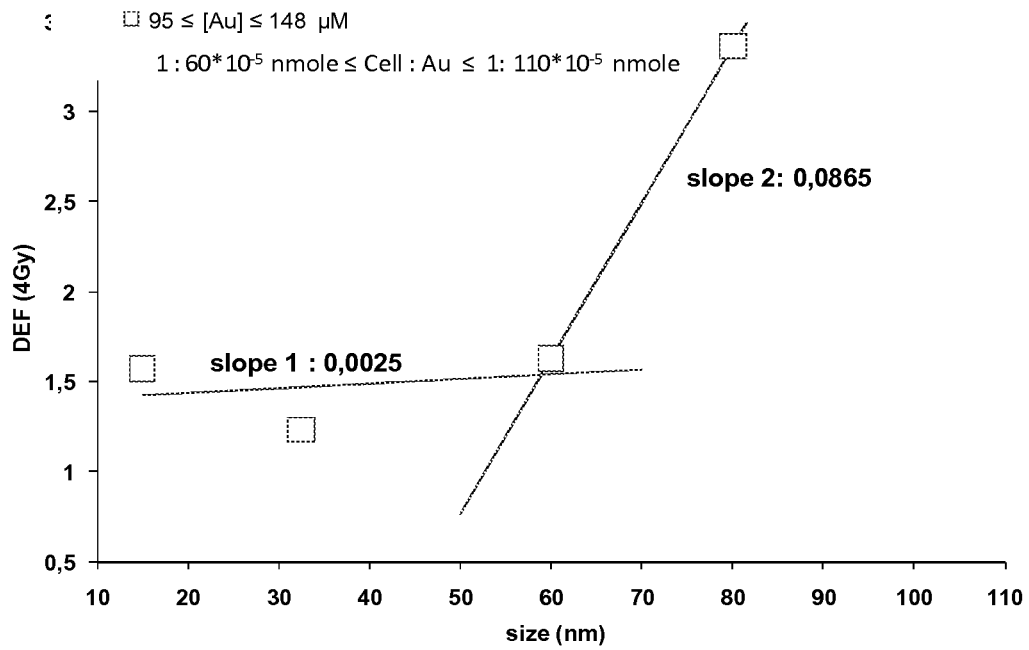

Gold (Au) concentration per target cell is expressed as follow:

Cell:Au=1:X (X is expressed in nmole)
Cell:Au≤1:15×10$^{-5}$: cross dots
1:20*10$^{-5}$ Cell:Au≤1:45×10$^{-5}$: diamond dots
1:60*10$^{-5}$ Cell:Au=1:110×10$^{-5}$: square dots
Cell:Au=1:182×10$^{-5}$: triangle dot FIGS. 5A and 5B:

FIG. 5A shows a threshold effect for a gold nanoparticle size ≥80 nm. The gold concentration at cellular level was between 20 μM and 83 μM.

The corresponding gold concentration per target cell was between 20×10$^{-5}$ nmole and 45×10$^{-5}$ nmole.

Two linear tendency curves are established with a significant difference between their respective slope values: gold nanoparticles with a size between 15 nm and 60 nm present a linear tendency curve with a slope of 0.0033. Gold nanoparticles with a size between 80 nm and 105 nm present a linear tendency curve with a slope of 0.0384. The slopes ratio revealed by said two curves is of about 10. The threshold effect observed when considering DEF is induced by the metallic nanoparticle size when said size is of about 80 nm or more.

FIG. 5B shows a threshold effect for gold nanoparticle size ≥80 nm. The gold concentration at cellular level was between 95 μM and 148 μM The corresponding gold concentration per target cell was between 60×10$^{-5}$ nmole and 110×10$^{-5}$ nmole.

Two linear tendency curves are established with a significant difference between their respective slope values: Gold nanoparticles with a size between 15 nm and 60 nm present a linear tendency curve with a slope of 0.0025. Gold nanoparticles with a size between 80 nm and 105 nm present a linear tendency curve with a slope of 0.0865. The slopes ratio revealed by said two curves is of about 30. The threshold effect observed when considering DEF is induced by the metallic nanoparticle size when said size is of about 80 nm or more.

Figure 6A:
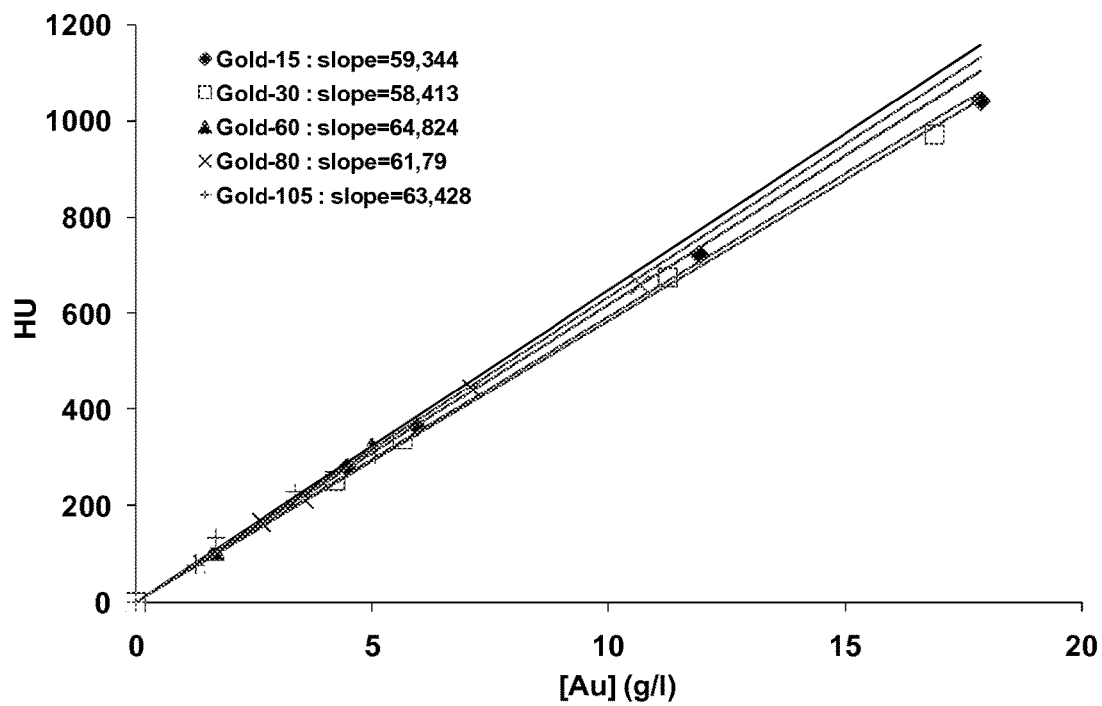
Figure 6B:
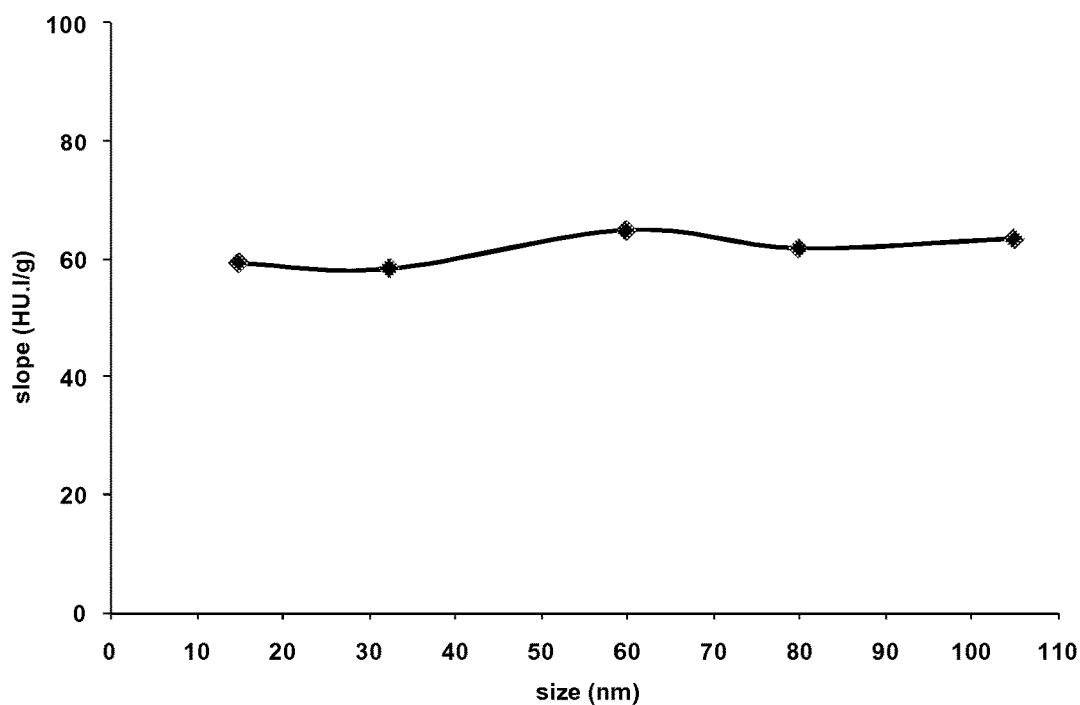

FIGS. 6A and 6B:

FIG. 6A shows the X-ray attenuation as a function of gold concentration for each gold nanoparticle described in example 1, Table 1.

HU value as a function of [Au] (g/L) for GOLD-15: diamond dots
HU value as a function of [Au] (g/L) for GOLD-30: square dots
HU value as a function of [Au] (g/L) for GOLD-60: triangle dots
HU value as a function of [Au] (g/L) for GOLD-80: cross dots
HU value as a function of [Au] (g/L) for GOLD-105: +dots FIG. 6B shows the impact of gold nanoparticle size on X-Rays attenuation. The slope for each size of gold nanoparticle is obtained from FIG. 6A and reported as a function of gold nanoparticle size.

Figure 7A:
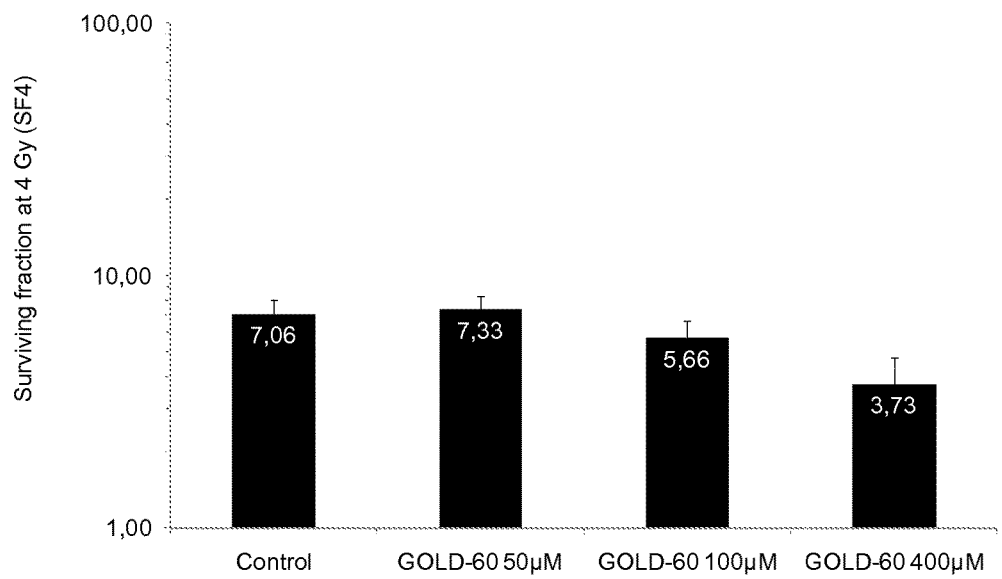
Figure 7B:
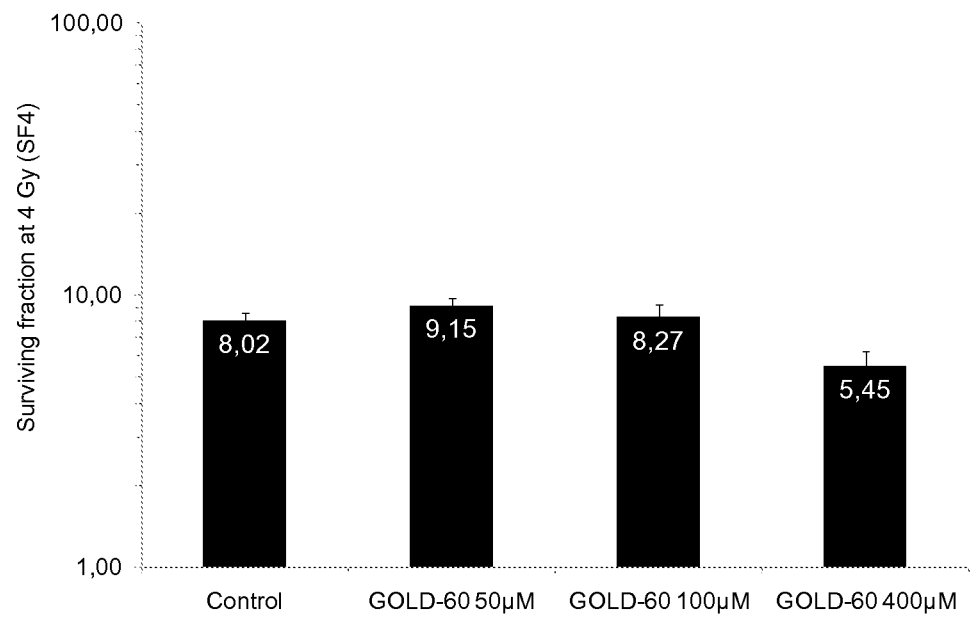

FIGS. 7A and 7B:

FIG. 7A shows the surviving fraction under a 4 Gy irradiation (SF4) of HT29 cells incubated with gold nanoparticles (GOLD-60 from example 1) for less than 5 minutes FIG. 7B shows the surviving fraction under a 4 Gy irradiation (SF4) of HT29 cells incubated with gold nanoparticles (GOLD-60 from example 1) for about 12 hours.

DETAILED DESCRIPTION OF THE INVENTION

It has been surprisingly found by inventors that a nanoparticle made of a metal, preferably a metal having an atomic number (Z) of at least 25, and having, as the largest size, a size comprised between about 80 and 105 nm, can substantially enhance the therapeutic effect of a local irradiation intended to disturb, alter or destroy abnormal cells, tissues or organs in an animal.

A strong enhancement of radiotherapy efficacy can be observed for the first time using metallic nanoparticles according to the present invention (cf. FIGS. 4A, 4B, 5A and 5B for example).

In the spirit of the invention, the term "nanoparticle" refers to products, in particular synthetic products, with a size in the nanometer range.

In the context of the present invention, the term size refers to the largest dimension of the metallic core of the nanoparticle. Typically, the largest dimension is the diameter of a nanoparticle of round or spherical shape, or the longest length of a nanoparticle of ovoid or oval shape.

The nanoparticle's shape can be for example round, flat, elongated, spherical, ovoid or oval, and the like. The shape can be determined or controlled by the method of production, and adapted by the person of the art according to the desired applications.

As the shape of the particles can influence their "biocompatibility", particles having a quite homogeneous shape are preferred. For pharmacokinetic reasons, nanoparticles being essentially spherical, round or ovoid in shape are thus preferred. Spherical or round shape is particularly preferred.

The largest size of the nanoparticles according to the invention is advantageously, as demonstrated by the experimental part, comprised between about 70 nm and about 130 nm, advantageously between about 75 or 80 nm and about 105 nm, preferably between about 75 nm and about 95 nm or between about 80 nm and about 90 or 95 nm.

Inventors surprisingly demonstrate for the first time that the nanoparticle penetration into the target cell, a tumor cell for example, is not required, in the context of the present invention, to perturb, destroy or alter said cell. Indeed, an equivalent effect on target cells has been observed by inventors in both conditions wherein nanoparticles have been incorporated by target cells or are in contact, in particular external contact, with said cells.

Inventors herein describe the use of a metallic nanoparticle as herein disclosed, or of a population of such metallic nanoparticles, to prepare a pharmaceutical composition intended to perturb, disturb, alter or destroy target mammalian cells when said cells are exposed to ionizing radiations. In said population, the nanoparticles are made of a metal, the metal having preferably an atomic number (Z) of at least 25. Advantageously, the mean largest size of the nanoparticles of the population is between about 70 nm and about 130 nm, advantageously between about 75 or 80 nm and about 105 nm, preferably between about 75 nm and about 95 nm or between about 80 nm and about 90 or 95 nm.

In a typical population of nanoparticles, as referred to previously, constituted by nanoparticles obtained according to a method of the art (as further described below), wherein the mean largest size of a nanoparticle of the population is between about 80 nm and about 105 nm, the largest size of a nanoparticle of the population is comprised between about 60 nm and 155 nm, typically between 60, 65, 70, 75, or 80, and, 105, 110, 130, 140, 150 or 155 nm.

In other words, 95% (2σ) of the population is made of nanoparticles the largest size of which is between about 60 nm and about 155 nm or 68% (1σ) of the population is made of nanoparticles the largest size of which is between about 70 nm and about 130 nm.

The metallic nanoparticles according to the present invention are made of a metal, said metal having preferably an atomic number of at least 25, advantageously at least 40 or 50, more preferably at least 60 or 70.

Such a metal may be selected from gold (Au—Z=79), silver (Ag—Z=47), platinum (Pt—Z=78), palladium (Pd—Z=46), tin (Sn—Z=50), tantalum (Ta—Z=73), ytterbium (Yb—Z=70), zirconium (Zr—Z=40), hafnium (Hf—Z=72), terbium (Tb—Z=65), thulium (Tm—Z=69), cerium (Ce—Z=58), dysprosium (Dy—Z=66), erbium (Er—Z=68), europium (Eu—Z=63), holmium (Ho—Z=67), iron (Fe—Z=26), lanthanum (La—Z=57), neonydium (Nd—Z=60), praseodynium (Pr—Z=59), and mixtures thereof.

The metal is preferably selected from gold (Au), silver (Ag), platinum (Pt), palladium (Pd), tin (Sn), zirconium (Zr) and iron (Fe).

The atomic number (also known as the proton number) is the number of protons found in the nucleus of an atom. It is traditionally represented by the symbol Z. The atomic number uniquely identifies a chemical element. In an atom of neutral charge, the atomic number is equal to the number of electrons.

Z participates to the incoming radiations absorption capacity of nanoparticles.

In a preferred embodiment of the present invention, the metallic nanoparticles are made of gold.

In the present invention, mixture of metals as identified previously in a particular nanoparticle, or in a particular population of nanoparticles, is also possible.

Nanoparticles having a low specific surface area (SSA) are further preferred in order to limit their interactions with the surrounding environment.

The Specific Surface Area (SSA) is a material property of solids which measures the total surface area per unit of mass (m2/g). SSA appears to be an important factor affecting the nanoparticle biological system interface; on an equal mass-dose basis, it has been reported that ultrafine particles cause more adverse effects, such as inflammation, when administered in an animal, than do fine particles (see for example Nel et al. (Nature Materials 8 (2009) 543).

Metallic nanoparticles, the largest size of which is between about 80 and 105 nm are particularly advantageous regarding SSA as explained below.

For the purpose of the present invention, the nanoparticle specific surface area is for example comprised between about 1 $m^2/g$ and 50 $m^2/g$. The specific surface area is preferentially comprised between 2 $m^2/g$ and 20 $m^2/g$.

The specific surface area of a spherical nanoparticle may be estimated using the following equation (SSA=3000/(d×r)), d being the density of the metallic nanoparticle, and r the radius of the nanoparticle.

Hence spherical gold nanoparticles with a particle size of 15, 30, 60, 80 and 100 nm will develop a specific surface area respectively of 20.7, 10.3, 5.2, 3.9 and 3.1 $m^2/g$, for a gold nanoparticle density of 19.32.

Spherical iron nanoparticles with a particle size of 15, 30, 60, 80 and 100 nm will develop a specific surface area respectively of 50.8, 25.4, 12.7, 9.5 and 7.6 $m^2/g$, for an iron nanoparticle density of 7.87.

Inventors herein disclose that the surprising efficiency of the nanoparticles according to the present invention is mainly due to their size. A nanoparticle, the size of which is of at least 80 nm, is indeed, when exposed to ionizing radiations, capable of generating more damages to target cells than is a nanoparticle of smaller size, in particular a nanoparticle of 60 nm or less. Inventors thus herein highlight the fundamental and direct influence of the nanoparticle size on cell disturbance under ionizing radiations, the herein described sizes favouring therapeutic applications in a mammal, when said size reaches, and preferably exceeds, the 80 nm threshold (see experimental part). The largest the nanoparticle size in the herein identified range of sizes, the more efficient is their ability to generate cell damages.

A possible explanation of this mechanism could be due to the nanoparticle ability to deliver the captured energy (ionizing radiation) in a better or different way.

In example 2 and 3, in order to differentiate the influence of gold nanoparticle size from the influence of gold concentration on the therapeutic effect induced by the nanoparticles under irradiation, in vitro assays were all performed by inventors using the gold nanoparticle size as unique adjustable parameter. The experimental results obtained by inventors revealed the surprising influence of the nanoparticle size (for a constant metal concentration) on the amplification of the therapeutic efficacy (ability to kill cells and/or to prevent cells to divide).

In order to produce an efficient therapeutic effect under ionizing radiations, the use of metallic nanoparticles with a nanoparticle size ≥80 nm requires a metal concentration per target cell which is between about 2 and 7 times, in particular between 4 and 7 times or between 2 and 5 times, inferior to the metal concentration per target cell required when using metallic nanoparticles with a nanoparticle size of about 60 nm or less (see examples 2 and 3 regarding GNPs).

A significant and advantageous reduction of the metal amount to be administered to the patient with a similar treatment efficiency, associated to a reduction of deleterious side effects, are therefore now possible thanks to the present invention.

The present invention further allows a significant reduction of the number of administration steps in the context of a radiotherapeutic treatment in particular, typically in the course of a multi fractionated protocol of irradiation as performed in clinic until now. Indeed, the nanoparticles described in the present patent application are large enough to favour their retention in a tumor tissue. A substantially decreased target tissue clearance of the metallic larger nanoparticles size has been observed in the literature (CHANG et al., Cancer Sci. 99 (2008) 1479; Hainfeld et al., Phys. Med. Biol 49 (2004) N309).

The required doses of ionizing radiations are preferably doses comprised between about 0.05 Gray and about 16 Grays, preferably between about 0.05 Gray and about 6 Grays, for applications performed in vitro.

Doses are comprised between more than about 0.05 Gray and less than about 16 or 30 Grays for applications performed, in particular locally, ex vivo or in vivo.

Total ionizing radiations range from about 1.5 Gray up to about 85 Grays in the human according to the current practice. Additional irradiation boost of about 40 Gray may also be provided in the human, according to the current practice.

The total dose of radiations delivered can be given following different schedules such as single dose, fractionated doses, hyperfractionated doses, etc.

Irradiated nanoparticles herein described provide, as demonstrated in the experimental section, a clear therapeutic effect improvement when compared to the effect obtained using irradiated nanoparticles of smaller sizes.

The nanoparticles according to the present invention are advantageously biocompatible, that is to say, they can be safely administered to an animal organism, typically a mammal, in particular a human, to provide their therapeutic effect. Said biocompatibility can be ensured for example by the nature of the metal(s) constituting the particle and/or by an optional coating.

Preferred nanoparticles according to the invention are covered with a biocompatible coating regardless of the route of administration. When the nanoparticles of the present invention are administered to a subject via the intravenous (IV) route, such a biocompatible coating is particularly advantageous to optimize the biodistribution of nanoparticles in the context of the previously described EPR effect. A full biocompatible coating of the nanoparticle is preferred, in particular in the IV context, in order to avoid interaction of the particle surface with any recognition element (macrophage, opsonins, etc.). The "full coating" implies the presence of a very high density of biocompatible molecules able to create at least a complete monolayer on the surface of the particle. Said coating is responsible for the so called "stealth effect" of the nanoparticle.

The biocompatible coating allows or favours (depending on the selected metal the nanoparticle is made of) in particular the nanoparticle stability in a biocompatible suspension, such as a physiological fluid (blood, plasma, serum, etc.), any isotonic media or physiologic medium, for example media comprising glucose (5%) and/or NaCl (0.9%), which is required for a pharmaceutical administration.

Such a biocompatible coating is obtained by treating the nanoparticle with a surface treating agent.

Stability may be confirmed by dynamic light scattering of the metallic nanoparticles in biocompatible suspension or by ICP-MS quantification of metal element prior and/or after filtration, of the metallic nanoparticles in biocompatible suspension, on a 0.22 μm filter.

Advantageously, said coating preserves the integrity of the particles in vivo, ensures or improves the biocompatibility thereof, and facilitates an optional functionalization thereof (for example with spacer molecules, biocompatible polymers, targeting agents, proteins, etc.). A particular nanoparticle according to the present invention indeed further comprises a surface component enabling specific targeting of biological tissues or cells. Such a surface component is preferably a targeting agent allowing the nanoparticle interaction with a recognition element present on the target cell. Such targeting agents can act once the nanoparticles are accumulated in the tumor. As the conformation of the targeting agent will be responsible for its interaction with the target, the density of said targeting agent is to be controlled carefully. A high density thereof can indeed perturb the targeting agent conformation and in consequence its recognition by the target cell (see for example J A Reddy et al. Gene therapy 9 (2002) 1542; Ketan B. Ghaghada et al. Journal of Controlled Release 104 (2005) 113). In addition, a high target agent density may favour nanoparticles clearance by the Reticulo Endothelial System (RES) during circulation in the vasculature.

The biocompatible coating can be composed of any amorphous or crystalline structure.

In general, the coating can be non-biodegradable or biodegradable. Both options can be used for the purpose of the present invention.

Examples of non-biodegradable coatings are one or more materials or surface treating agents selected in the group consisting of silica, alumina, sugar (agarose for example), phosphate, silane, thiol, zwitterionic compounds, lipids, saturated carbon polymers (polyethylene oxide for example) and inorganic polymers, reticulated or not, modified or not (polymethacrylate or polystyrene for example), as well as combinations thereof.

Examples of biodegradable coatings are for example one or more materials or surface treating agents selected from the group consisting of a biological molecule, modified or not, natural or not and a biological molecular polymer; modified or not, of natural shape or not. The biological polymer may be a phospholipid, a saccharide, an oligosaccharide or a polysaccharide, polysulfated or not, for example dextran.

The aforementioned materials, compounds or surface treating agents can be used alone or in combinations, mixtures or assemblies, composite or not, covalent or not, optionally in combination with other compounds. Moreover, it is also possible to use any one of the aforementioned material, said material being naturally water-soluble or lipid-soluble or being artificially modified to become water-soluble or lipid-soluble.

The biocompatible coating preferably comprises or is made of a compound selected in the group consisting of an inorganic agent, an organic agent, and a mixture or combination thereof.

Appropriate inorganic agent may be selected from the group consisting of an oxide, a hydroxide and an oxyhydroxide. The inorganic agent may comprise for example silicium, aluminium, calcium and/or magnesium.

Such agents can be used to charge the nanoparticle either positively or negatively in order to modulate interactions of said nanoparticle with the biological media.

An inorganic agent selected from the group consisting of, for example magnesium and calcium, will bring a positive charge to the surface of the nanoparticle at a pH of 7.

For example, the silicium may be used to bring a negative charge to the surface of the nanoparticle at a pH of 7.

An appropriate organic agent may be any agent comprising a function capable of interacting with a nanoparticle according to the present invention and a function conferring biocompatibility to said nanoparticle.

The agent comprising a function capable of interacting with a nanoparticle may be for example a carboxylate (R—COO$^-$), a silane (R—Si(OR)$_3$), a phosphonic function (R—PO(OH)$_2$), a phosphoric function (R—O—PO(OH)$_2$), or a thiol function (R—SH).

The agent comprising a function capable of conferring biocompatibility to a nanoparticle according to the present invention may have a steric function and/or an electrostatic function. Such agent with a steric function may be selected from the group consisting of polyethylene glycol (PEG), polyethylenoxide, Polyvinylalcohol, Polyacrylate, Polyacrylamide (poly(N-isopropylacrylamide)), Polycarbamide, a biopolymer or polysaccharide such as Dextran, Xylan, cellulose, collagene, and a zwitterionic compound such as polysulfobetain, etc.

Agent with a positive electrostatic function may be an amine such as aminopropyltriethoxisilane, polylysine or 2-aminoethanethiol.

Agent with a negative electrostatic function may be selected from the group consisting of phosphate (for example a polyphosphate, a metaphosphate, a pyrophosphate, etc.), carboxylate (for example citrate or dicarboxylic acid, in particular succinic acid) and thiol (for example a carboxy terminated thiol such as mercaptosuccinic acid).

The coating can also contain different functional groups (or linker segments), allowing any molecule of interest to bind to the surface of the particle, such as a surface component enabling specific targeting of biological tissues or cells.

A typical example of a nanoparticle according to the invention is a nanoparticle made of gold. Such a gold nanoparticle can comprise, in addition, as a biocompatible coating, a coating made of thiol compounds such as polyethyleneglycol-thiol (PEG-SH), thioglucose, or carboxylate compounds such has citrate.

Another example of a nanoparticle according to the invention is a nanoparticle made of gold comprising, as a biocompatible coating, a coating made of thiol agents bearing at least one functional group selected from polyethylene, amine or carboxyl, or a coating consisting in citrate.

The present nanoparticles offer the advantage of being easy to prepare. Methods of producing metallic nanoparticles are indeed well known in the art (see for example Brian L. Cushing et al. (Chem. Rev. 104 (2004) 3893). Typically, metallic nanoparticles are obtained by precipitation of a metallic element in an aqueous or a non-aqueous solution, said precipitation involving chemical reduction of the metallic cation. Another possible way of production of metallic nanoparticles is through radiation-assisted reduction.

Another object of the invention relates to a method of producing a metallic nanoparticle or population of metallic nanoparticles such as defined hereinabove, comprising:
  providing a metallic element as herein identified, preferably a metallic element having an atomic number (Z) equal to or above 25,
  preparing the metallic nanoparticle from said metallic element by precipitation of said metallic element in a medium, in the presence of a reducing agent, and, optionally
  adding a complexing agent to the medium (the complexing agent being added prior to, during or after the addition of the reducing agent), the reducing agent and the complexing agent being optionally the same compound, and, optionally,
  coating the nanoparticle using a surface treating agent as described previously.

A medium typically used in the present invention may be selected from an aqueous solution, an alcoholic solution, etc.

A reducing agent typically used may be selected from citrate, ascorbic acid, 2-mercaptosuccinic acid.

A complexing agent typically used may be selected from citrate, thiol such as 2-mercaptosuccinic acid, etc.

The coating step advantageously consists in placing the nanoparticle in contact with a surface treating agent as defined previously.

In a particular embodiment, a method of producing a population of nanoparticles comprises the following steps, preferably in order:
a) providing, as a precursor, a metallic element as herein identified, preferably a metallic element having an atomic number (Z) equal to or above 25,
b) Precipitating the precursor of step a) in a polar medium as defined previously in the presence of a reducing compound, by preferably adjusting the precursor and/or the reducing compound concentration and/or the temperature,
c) optionally adding a complexing agent in the polar medium, prior to, during or after the precipitation step b), the complexing agent and the reducing agent being optionally the same compound,
d) optionally washing the suspension obtained at the end of step b) or c) to remove any impurities, reducing agent and/or complexing agent,
e) optionally concentrating the suspension obtained at the end of step d), and
f) optionally coating the nanoparticles.

The population described above may be further submitted to a formulation step before being administered to a subject.

In a particular example, a method of producing a nanoparticle according to the present invention, the nanoparticle being made of a metal, preferably comprises the following steps in order:
a) precipitating a solution of gold chloride precursor (such as in particular $HAuCl_4$ or $KAuCl_4$) in aqueous solution in a presence of a reducing agent (such as citrate), the temperature of the medium being comprise between 50° C. and 100° C.,
b) optionally washing the obtained metallic nanoparticle suspension to remove any impurities, c) optionally concentrating the metallic nanoparticles suspension thus obtained,
d) optionally coating said metallic nanoparticles by placing them in contact with a surface treating agent as defined previously.

Another object of the invention is based on any composition comprising nanoparticles such as defined hereinabove and/or which can be obtained by the methods herein described. While not mandatory, the particles in the inventive compositions advantageously have quite homogeneous shape as indicated previously.

Biocompatible suspensions comprising a high concentration of metal element (300 g/L for example) can be obtained with a method as herein described.

A particular object of the invention relates to a pharmaceutical composition comprising nanoparticles such as defined hereinabove and, optionally, a pharmaceutically acceptable excipient or vehicle.

The compositions can be in the form of a solid, liquid (particles in suspension), aerosol, gel, paste, and the like. Preferred compositions are in the form of an injectable formulation, preferably in a liquid form.

The excipient or vehicle which is employed can be any classical support for this type of application, such as for example saline, isotonic, sterile, buffered solutions, and the like. They can also comprise stabilizers, sweeteners, surfactants, and the like. They can be formulated for example as ampoules, aerosol, bottles, tablets, capsules, by using known techniques of pharmaceutical formulation.

Advantageously, the metal concentration to be administered per target cell is between about $10^{-7}$ nmole (Cell:[metal]=$1:10^{-7}$ (nmole)) and about $5 \times 10^{-1}$ nmole (cell:[metal]=$1:5 \times 10^{-1}$ (nmole)). More preferably, the metal concentration per target cell is between about $10^{-6}$ nmole (Cell:[metal]=$1:10^{-6}$ (nmole)) and about $2 \times 10^{-1}$ nmole (cell:[metal]=$1:2 \times 10^{-1}$ (nmole)).

Even more preferably, the metal concentration per target cell is between about $10^{-6}$ nmole (Cell:[metal]=$1:10^{-6}$ (nmole)) and about $10^{-3}$ nmole (cell:[metal]=$1:10^{-3}$ (nmole)) or between about $10^{-6}$ nmole (Cell:[metal]=$1:10^{-6}$ (nmole)) and about $10^{-4}$ nmole (cell:[metal]=$1:10^{-4}$ (nmole)).

In the herein described compositions, appropriate or desirable concentrations of metal are comprised between about 1 mg and about 100 mg of metal per gram of target mammalian cells, such as, in particular, tumor mammalian cells, typically between about 1 mg or 5 mg and 50 mg of metal per gram of target mammalian cells.

Generally, the compositions in liquid form comprise between 0.01 g/L and 300 g/L of metal, preferably at least 1 g/L, 5 g/L, 10 g/L, 20 g/L, 40 g/L, 60 g/L, 80 g/L, 100 g/L, 150 g/L, 200 g/L or 250 g/L.

Metal quantification is ideally performed by ICP-MS.

The above identified metal concentrations vary depending of the patient subject, the selected route of administration, the nature of the target cells, etc., and are easily adjustable by the man of the art.

The nanoparticles, populations of nanoparticles and compositions of the invention are products which can be used in many fields, particularly in human or veterinary medicine.

It is an object of the present invention to use a product as herein described to alter, destroy a target cell, tissue or organ.

Depending on the energy of ionizing radiations, the particles can enable perturbation of cells and/or tissues, or destruction thereof.

Hence a particular object of the invention is based on the use of a metallic nanoparticle or a population of nanoparticles according to the present invention to prepare a pharmaceutical composition intended to alter, destroy target cells in an animal, when said cells are exposed to radiations, in particular to ionizing radiations, and on the corresponding therapeutic methods.

The pharmaceutical composition can further comprises an additional therapeutic compound, distinct from a nanoparticle or of a population of nanoparticles as herein described, also intended to treat cancer.

Another particular object of the invention is based on a method for inducing or causing the perturbation, lysis, apoptosis or destruction of target cells, in vitro, ex vivo or in vivo, comprising contacting cells, in particular target cells, with one or more nanoparticles such as defined hereinabove, during a period of time sufficient to allow the nanoparticles to interact with said cells and, exposing the cells to radiations, appropriate radiations being in particular ionizing radiations, preferably X-Rays, γ-Rays, radioactive isotopes and/or electron beams, said exposure inducing or causing the perturbation, lysis, apoptosis or destruction of said target cells.

The target cells can be any pathological cells, that is to say, cells involved in a pathological mechanism, for example proliferative cells, such as tumor cells, stenosing cells (fibroblast/smooth muscle cells), or immune system cells (pathological cell clones). A preferred application is based on the treatment (for example the destruction or functional alteration) of malignant cells or tissue.

In this regard, a particular object of the invention is based on the use of a nanoparticle, or a population of such nanoparticles, as defined hereinabove, for producing a pharmaceutical composition intended for the treatment in particular of a cancer, when used in combination with ionizing radiations (as defined previously).

The present disclosure further encompasses the use of a composition, nanoparticle or population of nanoparticles such as defined hereinabove to prevent or treat a cancer or to alleviate the symptoms of a cancer in an animal, when said cells are exposed to radiations, in particular to ionizing radiations as defined previously.

Another particular object of the invention is based on a method for inducing or causing the perturbation, lysis or destruction of target cells, in particular cancer cells, in vitro, ex vivo or in vivo, comprising contacting target cells with one or more nanoparticles such as defined hereinabove, during a period of time sufficient to allow the particles to interact with said cells, and, exposing the cells to radiations, in particular to ionizing radiations as defined previously, said exposure inducing or causing the perturbation, lysis or destruction of said cells.

Another object of the invention relates to a method for preventing or treating a disorder, in particular a cancer, or alleviating the symptoms of the disorder, in a subject or patient, comprising administering to the patient suffering from the disorder a nanoparticle, a population of nanoparticles or a composition such as defined hereinabove, in conditions allowing the nanoparticles to interact (be in contact) with the abnormal cells, in particular cancer cells, and subsequently treating the subject by exposing said subject to ionizing radiations, such irradiation leading to an alteration, disturbance or functional destruction of the patient's abnormal cells, thereby preventing or treating a cancer.

Classical cancer management systematically implies the concurrence of multimodality treatments (combination of radiotherapy and chemotherapy for example).

The herein described nanoparticles submitted to ionizing radiations, in the context of radiotherapy, can be used in association with a different cancer therapy protocol. Such a protocol can be selected from the group consisting of surgery, radiosurgery, chemotherapy, a treatment comprising administration of cytostatic(s), cytotoxic(s), a targeted therapy, a vaccine, and any other biological or inorganic product intended to treat cancer.

Surprisingly, the herein described nanoparticles can further be used in the context of radiotherapy alone with increased observed efficacy.

The invention can be used to treat any type of malignant tumor such as haematological tumors or malignancies, and solid tumors, in particular of epithelial, neuroectodermal or mesenchymal origin. In addition, nanoparticles can be used to treat a premalignant lesion or a specific benign disease where radiation therapy is classically used and/or indicated.

The invention is applicable, in the context of therapy, to primary tumors, or secondary invasions, loco-regional or distant metastases, and in the context of prophylaxis, in order to avoid secondary malignant central nervous system involvement such as the observed invasions (metastasis) from melanoma, lung cancer, kidney cancer, breast cancer, etc.

The nanoparticles can be used at any time throughout the anticancer treatment period. They can be administered for example as a neoadjuvant (before surgical intervention for cancer exeresis) or as an adjuvant (after surgery).

The nanoparticles can also be used for advanced tumors which cannot be surgically removed.

As herein explained, the irradiation can be applied at any time after administration of the particles, on one or more occasions, by using any currently available system of radiotherapy.

The nanoparticles herein described are in particular intended to be used to treat cancer where radiotherapy is a classical treatment. Such cancer may be selected in particular from the group consisting of skin cancer, including malignant neoplasms associated to AIDS, melanoma; central nervous system tumors including brain, stem brain, cerebellum, pituitary, spinal canal, eye and orbit; head and neck tumors; lung cancers; breast cancers; gastrointestinal tumors such as liver and hepatobiliary tract cancers, colon, rectum and anal cancers, stomach, pancreas, oesophagus cancer; male genitourinary tumors such as prostate, testis, penis and urethra cancers; gynecologic tumors such as uterine cervix, endometrium, ovary, fallopian tube, vagina and vulvar cancers; adrenal and retroperitoneal tumors; sarcomas of bone and soft tissue regardless the localization; lymphoma; myeloma; leukemia; and pediatric tumors such as Wilm's tumor, neuroblastoma, central nervous system tumors, Ewing's sarcoma, etc.

The particles can be activated within a large range of total dose of irradiation. Amounts and schedules (planning and delivery of irradiations in a single dose, or in the context of a fractioned or hyperfractioned protocol, etc.) is defined for any disease/anatomical site/disease stage patient setting/patient age (children, adult, elderly patient), and constitutes the standard of care for any specific situation.

The irradiation can be applied at any time after administration of the nanoparticles, on one or more occasions, by using any currently available system of radiotherapy. The nanoparticles can be administered by different routes such as local (intra-tumoral (IT) in particular), subcutaneous, intra venous (IV), intra-dermic, intra-arterial, airways (inhalation), intra peritoneal, intra muscular and oral route (per os). The nanoparticles can further be administered in an intracavity such as the virtual cavity of tumor bed after tumorectomy.

Repeated injections or administrations can be performed, when appropriate.

The term "treatment" denotes any action performed to correct abnormal functions, to prevent diseases, to improve pathological signs, such as in particular a reduction in the size or growth of an abnormal tissue, in particular of a tumor, a control of said size or growth, a suppression or destruction of abnormal cells or tissues, a slowing of disease progression, a disease stabilization with delay of cancer progression, a reduction in the formation of metastases, a regression of a disease or a complete remission (in the context of cancer for example), etc.

As indicated previously, appropriate radiations or sources of ionization are preferably ionizing radiations and can advantageously be selected from the group consisting of X-Rays, gamma-Rays, electron beams, ion beams and radioactive isotopes or radioisotopes emissions. X-Rays is a particularly preferred source of ionization.

Ionizing radiations are typically of about 2 KeV to about 25 000 KeV, in particular of about 2 KeV to about 6000 KeV (LINAC source), or of about 2 KeV to about 1500 KeV (such as a cobalt 60 source). Using a X-Rays source, particularly preferred ionizing radiations are typically of about 50 KeV to about 12 000 KeV, for example of about 50 KeV to about 6000 KeV.

In general and in a non-restrictive manner, the following X-Rays can be applied in different cases to activate the nanoparticles:
  X-Rays of 50 to 150 keV which are particularly efficient for a superficial target tissue;
  X-Rays (ortho voltage) of 200 to 500 keV which can penetrate a tissue thickness of 6 cm;
  X-Rays (mega voltage) of 1000 keV to 25,000 keV. For example the ionization of nanoparticles for the treatment of prostate cancer can be carried out via five focused X-Rays with an energy of 15,000 keV.

Radioactive isotopes can alternatively be used as a ionizing radiation source (named as curietherapy or brachytherapy). In particular, Iodine $I^{125}$ (t½=60.1 days), Palladium $Pd^{103}$ (t½=17 days), Cesium $Cs^{137}$ and Iridium $Ir^{192}$ can advantageously be used.

Immunoradionuclide (or immunoradiolabelled ligand) can also be used as a ionizing radiation source in the context of radioimmunotherapy. Suitable radionuclides for radioimmunotherapy may be, for example, selected from $^{131}I$, $^{186}Re$, $^{177}Lu$ or $^{90}Y$.

Charged particles such as proton beams, ions beams such as carbon, in particular high energy ion beams, can also be used as a ionizing radiation source and/or neutron beams.

Electron beams may also be used as a ionizing radiation source with energy comprised between 4 MeV and 25 Mev.

Specific monochromatic irradiation source could be used in order to selectively generate X-rays with an energy close to or corresponding to the desired X-ray absorption edge of the atom(s) of the metallic nanoparticle.

Preferentially sources of ionizing radiations may be selected from Linear Accelerator (LINAC), Cobalt 60 and brachytherapy sources.

The term "in combination" indicates that the sought-after effect is obtained when the cells, tissues or organs of interest, being in contact with the nanoparticles of the invention, are activated by the defined source. However, it is not necessary for the particles and Rays to be administered simultaneously, nor according to the same protocol.

The present disclosure further provides kits comprising any one or more of the herein-described nanoparticles or compositions. Typically, the kit comprises at least one nanoparticle or population of nanoparticles according to the present invention. Generally, the kit also comprises one or more containers filled with one or more of the ingredients of the pharmaceutical compositions of the invention. Associated with such container(s), a labelling notice providing instructions for using the products can be provided for using the nanoparticles, population of nanoparticles or compositions according to the present methods.

Other aspects and advantages of the invention will become apparent in the following examples, which are given for purposes of illustration and not by way of limitation.

EXPERIMENTAL SECTION

Example 1

Synthesis and Physico-Chemical Characterisation of Gold Nanoparticles with Different Sizes Gold nanoparticles are obtained by reduction of gold chloride with sodium citrate in aqueous solution. Protocol was adapted from G. Frens Nature Physical Science 241 (1973) 21.

In a typical experiment, $HAuCl_4$ solution is heated to boiling. Subsequently, sodium citrate solution is added. The resulting solution is maintained under boiling for an additional period of 5 minutes.

The nanoparticle size is adjusted from 15 up to 105 nm by carefully modifying the citrate versus gold precursor ratio (cf. Table 1).

The as prepared gold nanoparticles suspensions are then concentrated using an ultrafiltration device (Amicon stirred cell model 8400 from Millipore) with a 30 kDa cellulose membrane.

The resulting suspensions are ultimately filtered through a 0.22 μm cutoff membrane filter (PES membrane from Millipore) under laminar hood and stored at 4° C.

Gold content is determined by ICP-MS and expressed as [Au] in g/L.

Figure 1A:
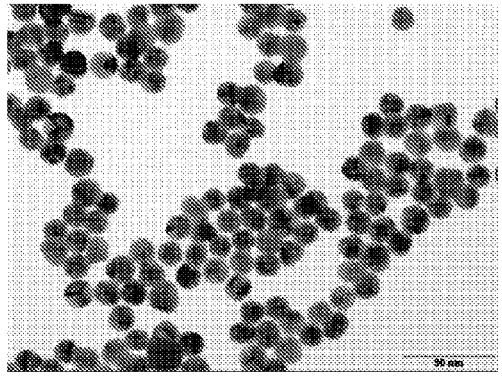
FIGS. 1A and 1B.
Figure 1A:
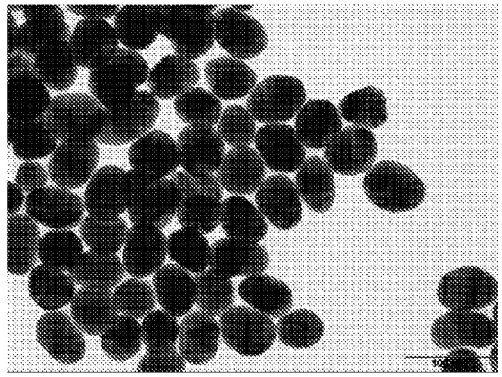
Figure 1A:
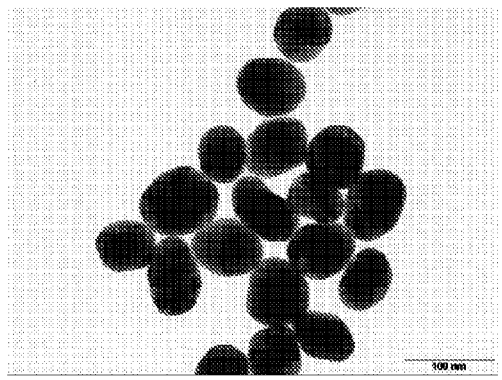
Figure 1A:
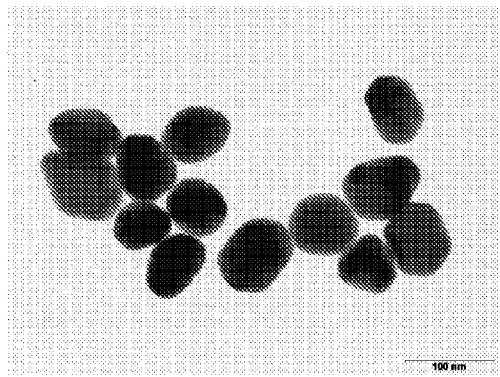
Figure 1B:
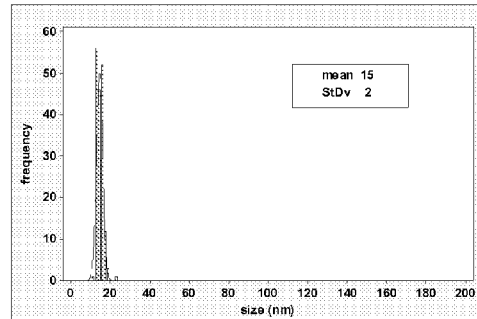
Figure 1B:
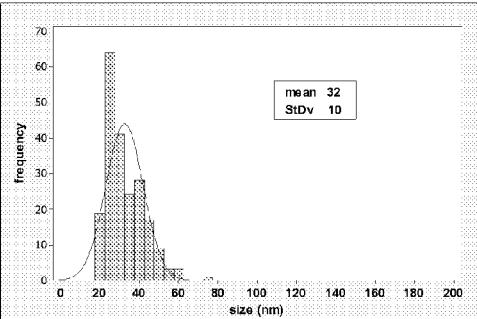
Figure 1B:
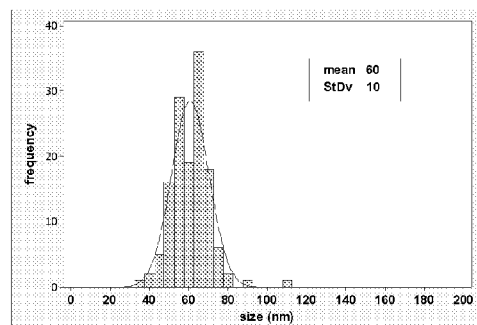
Figure 1B:
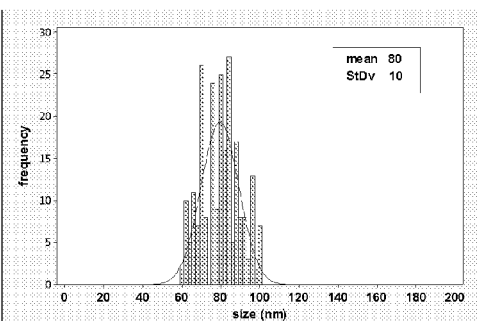
Figure 1B:
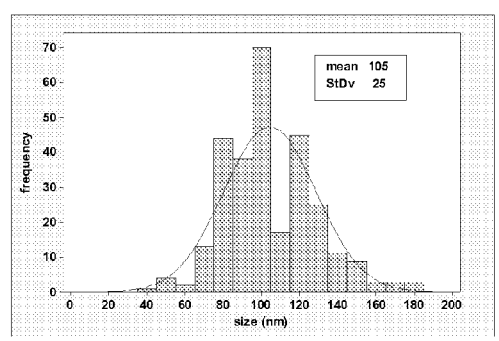
Figure 2A:
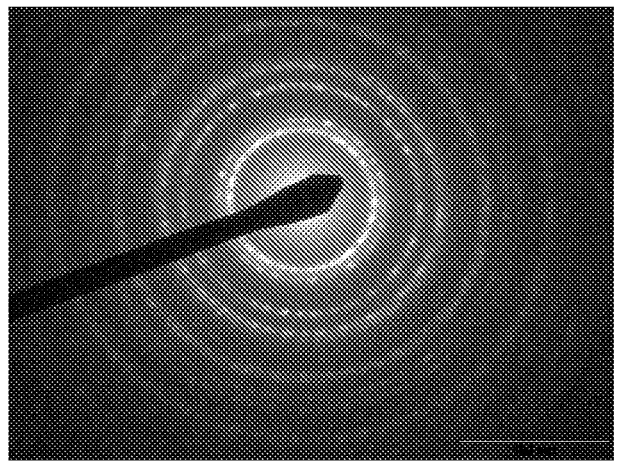
Figure 2A:
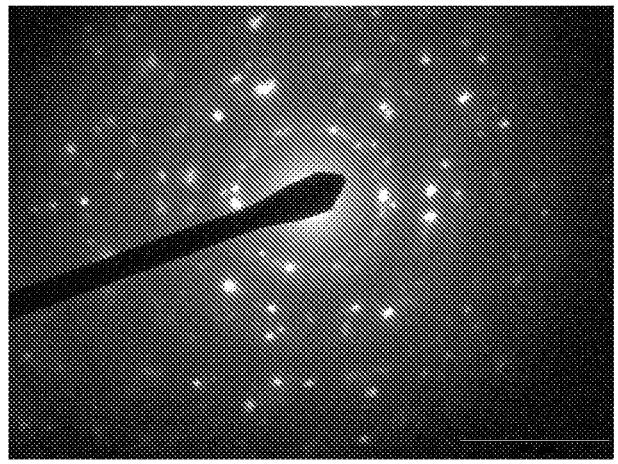

Particle size is determined using Transmission Electronic Microscopy (TEM) by counting more than 200 particles (FIG. 1A), taking the longest nanoparticle dimension for size measurement. Histograms are established and mean and standard deviation are reported (FIG. 1B).

Conclusion

The gold nanoparticles described in Table 1 are all prepared according to the same synthesis process to ensure the same surface characteristic properties.

The TEM images show that the synthesized gold nanoparticles are all spherical and/or ovoid in shape.

The TEM electronic diffraction patterns show that all the synthesized gold nanoparticles present a CFC structure.

Hence, only the size of the gold nanoparticle varies, with a well characterized mean particle size and a size polydispersity in accordance with prior art.

Example 2

Effect of Gold Nanoparticle Size on In Vitro Efficacy (Clonogenic Survival Assay) when the Gold Concentration is Constant at Cellular Level Protocol To investigate the enhancement of the radiation response of the gold nanoparticles (GNPs) which are internalized into the cell or bound to the cell (below expressed as gold concentration at cellular level), inventors used a specific clonogenic survival assay described below:

HT29 cells were plated at the density of 20 000 cells/cm². GNPs were added to the medium at various gold concentrations in the μM range. After an incubation time between 1 hours and 24 hours, the cell surpernatants were removed. Then, the cells were washed briefly with PBS to remove all GNPs non-attached or non-internalized into the cells. Inventors next performed cell trypsination and counted the cell number using Haemocytometer.

For each condition, inventors took a sample of 100000 cells/mL up to 220000 cells/mL further analysed for gold concentration by ICP-MS.

Gold (Au) concentration at cellular level (number of gold atoms per volume) is expressed in μM.

This parameter may also be expressed in term of gold (Au) concentration per target cell as follow:

cell:Au=1:X (X expressed in nmole)

according to the following calculation:

$$Cell = 1$$
$$X \text{ (expressed in } nmole\text{)} = \frac{\text{Gold (Au) concentration } (\mu M) \times 1 \text{ (mL)}}{1000 \text{ (mL)} \times \text{Number of cells per mL}}$$

The other cells were plated (at the density of 300 up to 1000 cells/wells according to the treatments conditions) to performed the clonogenic assays. Once the cells were attached to the plate, they were either non irradiated (sham control), or irradiated with doses of 2 Gy and 4 Gy using a 200 kVp X-Ray device. The cells were let to grown to form

TABLE 1

| | | Synthesis | | | |
|---|---|---|---|---|---|
| Samples | Particle size (nm) | Citrate | $HAuCl_4$ | Structure | [Au] g/L |
| Gold-15 | 15 ± 2 (1σ) | 20 mL 30 mM | 500 mL 0.25 mM | CFC | 17.86 |
| Gold-30 | 32 ± 10 (1σ) | 7.5 mL 40 mM | 500 mL 0.25 mM | CFC | 16.90 |
| Gold-60 | 60 ± 10 (1σ) | 2 mL 85 mM | 500 mL 0.25 mM | CFC | 4.98 |
| Gold-80 | 80 ± 10 (1σ) | 1.2 mL 43 mM | 200 mL 0.30 mM | CFC | 10.67 |
| Gold-105 | 105 ± 25 (1σ) | 1.2 mL 39 mM | 200 mL 0.33 mM | CFC | 5.06 | colonies up to 12 days. Then, the colonies were fixed and stained with crystal violet and counted in order to estimate clonogenic survival fraction (SF) (See FIGS. 3A and 3B) by using the following formulae:

Plating efficiency (PE) is the ratio of the number of colonies formed without any irradiation to the number of seeded cells:

$$PE = n° \text{ of colony formed} \times 100/n° \text{ of seeded cells}$$

Surviving fraction (SF) represents the level of viable cells after irradiation and is normalized to the PE of the control:

$$SF = n° \text{ of colonies formed after treatment}/(n° \text{ of cells seeded} * PE)$$

Dose Enhancement Factor (DEF) is estimated as the ratio of SF (radiation dose alone)/SF (gold nanoparticles activated with the same radiation dose).

TABLE 2

| GOLD SAMPLES | Gold (Au) concentration at cellular level (µM) Gold (Au) concentration per target cell Cell: Au = 1: X (X expressed in nmole) | | |
|---|---|---|---|
| | [Au] µM | Number of Cells per mL | Cell: Au = 1: X (nmole) |
| GOLD-15 | | | |
| GOLD-30 | | | |
| GOLD-60 | | | |
| GOLD-80 | | | |
| GOLD-105 | 6 | $1.6 \times 10^5$ | $3.6 \times 10^{-5}$ |
| GOLD-15 | 12 | $1.3 \times 10^5$ | $9.5 \times 10^{-5}$ |
| GOLD-30 | 17 | $1.3 \times 10^5$ | $13.1 \times 10^{-5}$ |
| GOLD-60 | 16 | $2.2 \times 10^5$ | $7.3 \times 10^{-5}$ |
| GOLD-80 | 17 | $2.0 \times 10^5$ | $8.5 \times 10^{-5}$ |
| GOLD-105 | 17 | $1.3 \times 10^5$ | $13.6 \times 10^{-5}$ |
| GOLD-15 | 20 | $9.7 \times 10^4$ | $20.7 \times 10^{-5}$ |
| GOLD-30 | 40 | $1.8 \times 10^5$ | $22.6 \times 10^{-5}$ |
| GOLD-60 | 83 | $2.2 \times 10^5$ | $37.7 \times 10^{-5}$ |
| GOLD-80 | 52 | $2.1 \times 10^5$ | $24.9 \times 10^{-5}$ |
| GOLD-105 | 59 | $1.4 \times 10^5$ | $43.4 \times 10^{-5}$ |
| GOLD-15 | 130 | $1.4 \times 10^5$ | $92.0 \times 10^{-5}$ |
| GOLD-30 | 148 | $1.4 \times 10^5$ | $108.3 \times 10^{-5}$ |
| GOLD-60 | 95 | $1.5 \times 10^5$ | $61.9 \times 10^{-5}$ |
| GOLD-80 | 119 | $1.8 \times 10^5$ | $65.4 \times 10^{-5}$ |
| GOLD-15 | | | |
| GOLD-30 | | | |
| GOLD-60 | 400 | $2.2 \times 10^5$ | $181.8 \times 10^{-5}$ |
| GOLD-80 | | | |
| GOLD-105 | | | |

Table 2 shows gold concentration at cellular level (µM) [or gold concentration per target cell (cell:Au=1:X (X expressed in nmole))] for different gold (Au) concentrations incubated with HT29 cancer cells for each gold nanoparticles synthesized in Example 1, Table 1.

TABLE 3A

| GOLD SAMPLES | Gold (Au) concentration at cellular level (µM) Gold (Au) concentration per target cell Cell: Au = 1: X (X expressed in nmole) | | | |
|---|---|---|---|---|
| | [Au] µM | Number of cells per mL | Cell: Au = 1: X (nmole) | DEF (4 Gy) |
| GOLD-15 | 12 | $1.3 \times 10^5$ | $9.5 \times 10^{-5}$ | 0.98 |
| GOLD-30 | 17 | $1.3 \times 10^5$ | $13.1 \times 10^{-5}$ | 0.99 |
| GOLD-60 | 16 | $2.2 \times 10^5$ | $7.3 \times 10^{-5}$ | 1.09 |
| GOLD-80 | 17 | $2.0 \times 10^5$ | $8.5 \times 10^{-5}$ | 0.98 |
| GOLD-105 | 17 | $1.3 \times 10^5$ | $13.6 \times 10^{-5}$ | 1.35 |

Table 3A reports the DEF values obtained for a 4 Gy irradiation dose, of the gold nanoparticles described in example 1, when gold concentration at cellular level is below 20 µM [or corresponding gold concentration per target cell is below $15*10^{-5}$ nmole (Cell:Au≤1:15*10$^{-5}$ nmole)].

TABLE 3B

| GOLD SAMPLES | Gold (Au) concentration at cellular level (µM) Gold (Au) concentration per target cell Cell: Au = 1: X (X expressed in nmole) | | | |
|---|---|---|---|---|
| | [Au] µM | Number of cells per mL | Cell: Au = 1: X (nmole) | DEF (4 Gy) |
| GOLD-15 | 20 | $9.7 \times 10^4$ | $20.7 \times 10^{-5}$ | 0.96 |
| GOLD-30 | 40 | $1.8 \times 10^5$ | $22.6 \times 10^{-5}$ | 1.16 |
| GOLD-60 | 83 | $2.2 \times 10^5$ | $37.7 \times 10^{-5}$ | 1.13 |
| GOLD-80 | 52 | $2.1 \times 10^5$ | $24.9 \times 10^{-5}$ | 1.63 |
| GOLD-105 | 59 | $1.4 \times 10^5$ | $43.4 \times 10^{-5}$ | 2.59 |

Table 3B reports the DEF values obtained for a 4 Gy irradiation dose, of the gold nanoparticles described in example 1, when gold concentration at cellular level is between 20 µM and 83 µM [or corresponding gold concentration per target cell is between $20 \times 10^{-5}$ nmole and $45 \times 10^{-5}$ nmole ($1:20 \times 10^{-5}$ nmole≤Cell:Au≤$1:45 \times 10^{-5}$ nmole)].

TABLE 3C

| GOLD SAMPLES | Gold (Au) concentration at cellular level (µM) Gold (Au) concentration per target cell Cell: Au = 1: X (X expressed in nmole) | | | |
|---|---|---|---|---|
| | [Au] µM | Number of cells per mL | Cell: Au = 1: X (nmole) | DEF (4 Gy) |
| GOLD-15 | 130 | $1.4 \times 10^5$ | $92.0 \times 10^{-5}$ | 1.57 |
| GOLD-30 | 148 | $1.4 \times 10^5$ | $108.3 \times 10^{-5}$ | 1.23 |
| GOLD-60 | 95 | $1.5 \times 10^5$ | $61.9 \times 10^{-5}$ | 1.63 |
| GOLD-80 | 119 | $1.8 \times 10^5$ | $65.4 \times 10^{-5}$ | 3.36 |

Table 3C reports the DEF values obtained for a 4 Gy irradiation dose, of the gold nanoparticles described in example 1, when gold concentration at cellular level is between 95 µM and 148 µM [or corresponding gold concentration per target cell is between $60 \times 10^{-5}$ nmole and $110 \times 10^{-5}$ nmole ($1:60 \times 10^{-5}$ nmole≤Cell:Au≤$1:110 \times 10^{-5}$ nmole)].

Conclusion

Surprisingly, a threshold in the DEF value is observed for gold nanoparticles with particle size ≥80 nm (see FIGS. 5A and 5B).

Example 3

Effect of Gold Nanoparticle Size on In Vitro Efficacy when the X-Ray Attenuation Capacity of Each Tested Gold Nanoparticle is Constant at Cellular Level Protocol: X-Ray Attenuation Measurement Gold nanoparticles with different gold concentration (expressed in [Au] g/L) were prepared in 200 µL tubes and placed in a custom-designed polystyrene holder.

µCT was performed using a General Electric Locus µCT system with anode voltage and current of respectively 50 KV and 450 µA.

Scanning was performed using a 90 µm isotropic resolution mode.

A cylindrical small region of interest was carefully placed in the 3D image over the center of each tube to measure attenuation values of fluid-filled tubes containing gold nanoparticles dispersions.

Conclusion

A similar X-rays attenuation value is observed whatever the gold nanoparticle size, for size comprised between 15 nm and 105 nm (see FIGS. 6A and 6B). This result confirms the threshold effect on efficacy observed for a nanoparticle size ≥80 nm. Such a nanoparticle is able to generate more damages at cellular level for a given absorbed X-Ray energy (see FIGS. 4A and 4B).

Example 4

Effect of Gold Nanoparticle Localization at Cellular Level (Physical Interaction with Tumor Cell Membranes and/or Cell Uptake) on In Vitro Efficacy HT29 cells are plated with the appropriate cells number to form between 50 and 200 colonies according to the treatment. When cells are attached, 50 µM, 100 µM or 400 µM of gold are added with an incubation time of less than 5 minutes (no incubation) or 12 hours. Gold nanoparticle with particle size of 60 nm (GOLD-60 from example 1) were tested. Cells were either non irradiated (sham control), or irradiated with doses of 2 Gy and 4 Gy using a 200 kVp X-Ray device. After irradiation, cells were incubated between 10 to 12 days at 37° C. The clones were fixed and stained with crystal violet and counted to estimate clonogenic survival fraction.

FIG. 7A shows the surviving fraction at 4 Gy (SF4) of HT29 cells incubated with gold nanoparticles (GOLD-60 from example 1) for less than 5 minutes, and FIG. 7B shows the surviving fraction at 4 Gy (SF4) of HT29 cells incubated with gold nanoparticles (GOLD-60 from example 1) for about 12 hours.

TABLE 4

| DEF GOLD-60 | 50 µM | 100 µM | 400 µM |
|---|---|---|---|
| 4 Gy, incubation time less than 5 mn | 0.96 | 1.25 | 1.8 |
| 4 Gy, incubation time 12 hours | 0.88 | 1 | 1.5 |

Table 4 presents the DEF of gold nanoparticle (GOLD-60) for gold concentration of 50 µM, 100 µM and 400 µM, at 4 Gy, for an incubation time of less than 5 nm or of 12 hours.

Conclusion

The data show, for a gold concentration of 400 µM, similar significant DEF values for gold nanoparticles incubated less than 5 minutes and for gold nanoparticles incubated 12 hours with cells prior irradiation.

These results demonstrate that gold nanoparticles (GNPs) enhance the target cell radiation response without it being necessary for the GNPs to be internalized by the cell. Indeed, and as known by the man of the art, two hours are necessary to allow the cell uptake of about 50% of the nanoparticles present in the biological medium (see Chitrani et al., 2006, for example).

When gold nanoparticles are in contact with cancer cells they are advantageously able to induce cancer cell damages under irradiation.

The above experimental results of examples 1 to 4 highlight the ability of metallic nanoparticles to induce an enhanced therapeutic effect when administered in vivo if an adequate metal concentration (proportional to the tumor weight as apparent to the man of the art) is present on the tumor site (the metallic nanoparticles cell uptake is not required as demonstrated previously).

A significantly smaller amount of metal is required per target cell, when using metallic nanoparticles with a particle size ≥80 nm when compared to the metal amount required when using metallic nanoparticles with a particle size of about 60 nm, to produce an efficient therapeutic effect when metallic nanoparticles are exposed to ionizing radiations (via radiotherapy for example).

In order to produce an efficient therapeutic effect under ionizing radiations, the use of metallic nanoparticles with a nanoparticle size ≥80 nm requires a metal concentration per target cell which is between about 2 and 7 times, in particular between 4 and 7 times or between 2 and 5 times, inferior to the metal concentration per target cell required when using metallic nanoparticles with a nanoparticle size of about 60 nm or less.

Such metallic nanoparticles appear advantageous for in vivo uses.

A population of metallic nanoparticles wherein the mean largest size of a nanoparticle of the population is between 80 and 105 nm, is particularly advantageous in therapy when said nanoparticles are exposed to ionizing radiations. Such nanoparticles indeed, in particular, allow an enhanced Dose Enhancement Factor (DEF). A threshold effect is observed in vitro for a nanoparticle as herein described the largest size of which is preferably ≥80 nm, and even more preferably between about 80 nm and 105 nm. Such a nanoparticle exhibits a reduced surface area allowing an improved biocompatibility and in consequence a reduced toxicity.

A population of metallic nanoparticles as herein described further allows a reduced tumor clearance. A single injection of a composition according to the present invention now allows the required therapeutic effect in the context of a multi fractionated irradiation protocol as currently applied in clinic.

REFERENCES

'Gold microspheres: a selective technique for producing biologically effective dose enhancement', Herold et Al., *Int. J. Rad. Biol.*, 2000, 76, pp 1357-1364

'Increased apoptotic potential and dose-enhancing effect of gold nanoparticles in combination with single-dose clinical electron beams on tumor-bearing mice', Meng-Ya Chang et Al., *Cancer Sci.*, 2008, 99(7) pp 1479-1484

'Elucidating the Mechanism of Cellular Uptake and Removal of Protein-Coated Gold Nanoparticles of Different Sizes and Shapes', B. Devika Chithrani et Al., *Nano Lett.*, 2007, 7 (6), pp 1542-1550

'Determining the Size and Shape Dependence of Gold Nanoparticle Uptake into Mammalian Cells', B. Devika Chithrani et Al., *Nano Lett.*, 2006, 6 (4), pp 662-668

'Enhancement of Radiation Cytotoxicity in Breast-Cancer Cells by Localized—Attachment of Gold Nanoparticles', Tao Kong et Al., *Small*, 2008, 4(9), pp 1537-1543

'Understanding biophysicochemical interactions at the nano-bio interface', Andre E. Nel et Al., *Nature Materials*, 2009, 8, pp 543-557

The use of gold nanoparticles to enhance radiotherapy in mice', James F Hainfeld et Al., *Phys. Med. Biol.*, 2004, 49, pp N309-N315

'Recent Advances in the Liquid-Phase Syntheses of Inorganic Nanoparticles', Brian L. Cushing et Al., *Chem. Rev.*, 2004, 104, pp 3893-3946

"Folate-targeted, cationic liposome-mediated gene transfer into disseminated peritoneal tumors'; J A Reddy et Al., *Gene therapy*, 2002, 9, pp 1542-1550

'Folate targeting of drug carriers: A mathematical model', Ketan B. Ghaghada et Al., *Journal of Controlled Release*, 2005, 104, pp 113-128

'Controlled Nucleation for the Regulation of the Particle Size in Monodisperse Gold Suspensions', G. Frens, *Nature Physical Science*, 1973, 241, pp 21-22.

The invention claimed is:

1. A method for inducing in vitro, ex vivo or in vivo the perturbation, lysis or destruction of target human cells selected from the group consisting of benign cells, pre-malignant cells and malignant cells, comprising i) contacting said target cells with a population of metallic nanoparticles having a constant metal concentration per target cell, during a period of time sufficient to allow the nanoparticles to interact with said cells, each nanoparticle of the population being made of a metal having an atomic number (Z) of at least 25, each metallic nanoparticle of the population being covered with a biocompatible coating, and the mean largest size of the nanoparticles of the population being between 80 and 105 nm, and, ii) exposing the cells to ionizing electromagnetic radiation, said exposure inducing or causing the perturbation, lysis or destruction of said cells.

2. The method according to claim 1, wherein the metal is selected from gold (Au), Silver (Ag), platinum (Pt), palladium (Pd), tin (Sn), Zirconium (Zr), or Iron (Fe).

3. The method according to claim 2, wherein the population of metallic nanoparticles comprises between $10^{-6}$ nmole and $10^{-3}$ nmole of metal per target cell.

4. The method according to claim 1, wherein said metallic nanoparticles comprises a surface component enabling specific targeting of biological tissues or cells.

5. The method according to claim 1, wherein each metallic nanoparticle is essentially spherical or ovoid in shape.

6. The method according to claim 1, wherein said ionizing electromagnetic radiation is selected from the group consisting of X rays and γ-rays.

7. The method according to claim 6, wherein said ionizing electromagnetic radiation is between 50 KeV to 12 000 KeV.

8. The method according to claim 6, wherein said ionizing electromagnetic radiation is X-ray radiation between 50 KeV to 6000 KeV.

9. The method according to claim 1, wherein said malignant cells are cells from a solid tumor.

10. The method according to claim 1, wherein said target human cells are also exposed to an additional therapeutic compound, distinct from the population of metallic nanoparticles, intended to treat cancer.

11. A method for treating a disorder or alleviating symptoms of the disorder, in a human patient having abnormal cells, comprising i) administering to the human patient suffering from the disorder a population of nanoparticles, in conditions allowing the nanoparticles to interact with the abnormal cells, each nanoparticle of the population being made of a metal having an atomic number (Z) of at least 25, each metallic nanoparticle of the population being covered with a biocompatible coating, and the mean largest size of the nanoparticles of the population being between 80 and 105 nm, said population of metallic nanoparticles having a constant metal concentration per target cell, and ii) subsequently treating the patient by exposing said patient to ionizing electromagnetic radiation, said exposition leading to an alteration, disturbance or functional destruction of the patient's abnormal cells, thereby preventing or treating the disorder or alleviating the symptoms of the disorder.

12. The method according to claim 1, wherein the biocompatible coating is a non-biodegradable coating selected from the group consisting of silica, alumina, sugar, phosphate, silane, thiol, zwitterionic compound, lipid, saturated carbon polymer and an inorganic polymer; or a biodegradable coating selected from the group consisting of biological polymer, phospholipid, saccharide, oligosaccharide and polysaccharide.

13. A pharmaceutical composition intended to alter or destroy target cells in a human when said cells are exposed to ionizing electromagnetic radiation, said pharmaceutical composition comprising a population of metallic nanoparticles and a pharmaceutically acceptable excipient, wherein each nanoparticle is made of a metal having an atomic number (Z) of at least 25, the mean largest size of the nanoparticles of the population is between 80 and 105 nm, said population of metallic nanoparticles having a constant metal concentration per target cell.

* * * * *